US012662536B2

(12) United States Patent
Yang et al.

(10) Patent No.: US 12,662,536 B2
(45) Date of Patent: Jun. 23, 2026

(54) BISPECIFIC ANTIBODY TARGETING CD3 AND CD20 AND USE THEREOF

(71) Applicants: Yang Yang, Yangpu (CN); Wei Yin, Yangpu (CN)

(72) Inventors: Yang Yang, Yangpu (CN); Wei Yin, Yangpu (CN)

( * ) Notice: Subject to any disclaimer, the term of this patent is extended or adjusted under 35 U.S.C. 154(b) by 1138 days.

(21) Appl. No.: 17/636,440

(22) PCT Filed: Jul. 23, 2020

(86) PCT No.: PCT/CN2020/103731
§ 371 (c)(1),
(2) Date: Feb. 18, 2022

(87) PCT Pub. No.: WO2021/031784
PCT Pub. Date: Feb. 25, 2021

(65) Prior Publication Data
US 2022/0298242 A1 Sep. 22, 2022

(30) Foreign Application Priority Data
Aug. 19, 2019 (CN) .......................... 201910764107.6

(51) Int. Cl.
*C07K 16/28* (2006.01)
*A61P 35/02* (2006.01)
*C07K 16/46* (2006.01)
*A61K 39/00* (2006.01)

(52) U.S. Cl.
CPC .......... *C07K 16/2809* (2013.01); *A61P 35/02* (2018.01); *C07K 16/2887* (2013.01); *C07K 16/468* (2013.01); *A61K 2039/505* (2013.01); *C07K 2317/31* (2013.01); *C07K 2317/55* (2013.01); *C07K 2317/73* (2013.01); *C07K 2317/92* (2013.01)

(58) Field of Classification Search
CPC ............ C07K 16/2809; C07K 16/2887; C07K 2317/31
USPC ....................................................... 424/136.1
See application file for complete search history.

(56) References Cited

U.S. PATENT DOCUMENTS

| | | | |
|---|---|---|---|
| 9,657,102 B2 | 5/2017 | Smith et al. | |
| 2013/0078249 A1 | 3/2013 | Ast et al. | |
| 2016/0145354 A1 | 5/2016 | Bacac et al. | |
| 2021/0380710 A1* | 12/2021 | Chen .................. | C07K 16/2809 |

FOREIGN PATENT DOCUMENTS

| | | | |
|---|---|---|---|
| CN | 102369215 A | | 3/2012 |
| CN | 104640562 A | | 5/2015 |
| CN | 105143270 A | | 12/2015 |
| CN | 108059680 A | | 5/2018 |
| CN | 109836502 A | | 6/2019 |
| CN | 110041429 A | | 7/2019 |
| CN | 110540593 A | | 12/2019 |
| IN | 103748114 A | | 4/2014 |
| WO | 2015/006749 | * | 1/2015 |
| WO | 2017167919 A1 | * | 10/2017 |

OTHER PUBLICATIONS

Edwards et al., J Mol Biol 334:103-118 (2003).*
Marchalonis et al., Dev & Comp Immunol. 30:223-247 (2006).*
Lippow et al., Nature Biotechnology, 25(10):1171-1176 (2007).*
Sulea et al., Scientific Reports, 8(260):1-11 (2018).*
Hasegawa et al., MABS, vol. 9, No. 5, pp. 854-873 (2017).*
Altshuler et al., Biochemistry (Moscow), 75(13):1584-1605 (2010).*
Vajda et al., Current Opinion in Structural Biology, 67 pp. 226-231 (2021).*
Marks et al., J. Biol. Chem. 295(29) 9823-9837 (2020).*
Akbar et al., Cell Reports 34, 108856, Mar. 16, 2021.*
Lo et al., BMC Genomics vol. 22, Article No. 116 (2021).*
Lu et al., "Tetravalent Anti-CD20/CD3 Bispecific Antibody for the Treatment of B Cell Lymphoma," Biochemical and Biophysical Research Communications (2016), vol. 473, pp. 808-813.
International Search Report (PCT/ISA/210) mailed on Oct. 29, 2020 for International Application No. PCT/CN2020/103731 (English Translation).
International Search Report (PCT/ISA/210) mailed on Mar. 4, 2021 for International Application No. PCT/CN2020/103731 (English Translation).
Written Opinion (PCT/ISA/237) mailed on Mar. 4, 2021 for International Application No. PCT/CN2020/103731.

* cited by examiner

*Primary Examiner* — Lynn A Bristol

(74) *Attorney, Agent, or Firm* — Zaher Li PLLC; Shawn S. Li

(57) ABSTRACT

The present invention provides an anti-CD3 single chain Fab molecule and an anti-CD20 single chain Fab molecule and their use in preparation of a bispecific antibody. The present invention also provides a bispecific antibody targeting CD3 and CD20 and its use in preparation of a medicament for treatment of a B-cell related disease.

2 Claims, 6 Drawing Sheets

Specification includes a Sequence Listing.

a b

SEQUENCE LISTING

<160> NUMBER OF SEQ ID NOS: 11

<210> SEQ ID NO 1
<211> LENGTH: 26
<212> TYPE: PRT
<213> ORGANISM: Artificial
<220> FEATURE:
<223> OTHER INFORMATION: Linking peptide

<400> SEQUENCE: 1

Gly Gly Gly Ser Gly Gly Ser Gly Gly Ser Gly Gly Ser Gly Gly Ser
1               5                   10                  15

Gly Gly Ser Gly Gly Ser Gly Gly Ser Gly
            20                  25

<210> SEQ ID NO 2
<211> LENGTH: 32
<212> TYPE: PRT
<213> ORGANISM: Artificial
<220> FEATURE:
<223> OTHER INFORMATION: Linking peptide

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

<210> SEQ ID NO 3
<211> LENGTH: 45
<212> TYPE: PRT
<213> ORGANISM: Artificial
<220> FEATURE:
<223> OTHER INFORMATION: Linking peptide

<400> SEQUENCE: 3

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 4
<211> LENGTH: 60

```
<212> TYPE: PRT
<213> ORGANISM: Artificial
<220> FEATURE:
<223> OTHER INFORMATION: Linking peptide

<400> SEQUENCE: 4

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 5
<211> LENGTH: 80
<212> TYPE: PRT
<213> ORGANISM: Artificial
<220> FEATURE:
<223> OTHER INFORMATION: Linking peptide

<400> SEQUENCE: 5

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

<210> SEQ ID NO 6
<211> LENGTH: 718
<212> TYPE: PRT
<213> ORGANISM: Artificial
<220> FEATURE:
<223> OTHER INFORMATION: CD3-binding moiety

<400> SEQUENCE: 6

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
```

-continued

```
        130                135                140

Val Gln Trp Lys Val Asp Asn Ala Leu Gln Ser Gly Asn Ser Gln Glu
145                150                155                160

Ser Val Thr Glu Gln Asp Ser Lys Asp Ser Thr Tyr Ser Leu Ser Ser
                165                170                175

Thr Leu Thr Leu Ser Lys Ala Asp Tyr Glu Lys His Lys Val Tyr Ala
                180                185                190

Cys Glu Val Thr His Gln Gly Leu Ser Ser Pro Val Thr Lys Ser Phe
                195                200                205

Asn Arg Gly Glu Cys Gly Gly Gly Ser Gly Gly Gly Gly Ser Gly
        210                215                220

Gly Gly Gly Ser Gly Gly Gly Gly Ser Gly Gly Gly Gly Ser Gly Gly
225                230                235                240

Gly Gly Ser Gly Gly Gly Gly Ser Gly Gly Gly Gly Ser Gly Gly Gly
                245                250                255

Gly Ser Gly Gly Gly Gly Ser Gly Gly Gly Gly Ser Gly Gly Gly Gly
                260                265                270

Ser Asp Ile Lys Leu Gln Gln Ser Gly Ala Glu Leu Ala Arg Pro Gly
        275                280                285

Ala Ser Val Lys Met Ser Cys Lys Thr Ser Gly Tyr Thr Phe Thr Arg
        290                295                300

Tyr Thr Met His Trp Val Lys Gln Arg Pro Gly Gln Gly Leu Glu Trp
305                310                315                320

Ile Gly Tyr Ile Asn Pro Ser Arg Gly Tyr Thr Asn Tyr Asn Gln Lys
                325                330                335

Phe Lys Asp Lys Ala Thr Leu Thr Thr Asp Lys Ser Ser Ser Thr Ala
                340                345                350

Tyr Met Gln Leu Ser Ser Leu Thr Ser Glu Asp Ser Ala Val Tyr Tyr
                355                360                365

Cys Ala Arg Tyr Tyr Asp Asp His Tyr Cys Leu Asp Tyr Trp Gly Gln
        370                375                380

Gly Thr Thr Leu Thr Val Ser Ser Ala Ser Thr Lys Gly Pro Ser Val
385                390                395                400

Phe Pro Leu Ala Pro Cys Ser Arg Ser Thr Ser Glu Ser Thr Ala Ala
                405                410                415

Leu Gly Cys Leu Val Lys Asp Tyr Phe Pro Glu Pro Val Thr Val Ser
                420                425                430

Trp Asn Ser Gly Ala Leu Thr Ser Gly Val His Thr Phe Pro Ala Val
                435                440                445

Leu Gln Ser Ser Gly Leu Tyr Ser Leu Ser Ser Val Val Thr Val Pro
        450                455                460

Ser Ser Ser Leu Gly Thr Lys Thr Tyr Thr Cys Asn Val Asp His Lys
465                470                475                480

Pro Ser Asn Thr Lys Val Asp Lys Arg Val Glu Ser Lys Tyr Gly Pro
                485                490                495

Pro Cys Pro Pro Cys Pro Ala Pro Glu Phe Leu Gly Gly Pro Ser Val
                500                505                510

Phe Leu Phe Pro Pro Lys Pro Lys Asp Thr Leu Met Ile Ser Arg Thr
                515                520                525

Pro Glu Val Thr Cys Val Val Val Asp Val Ser Gln Glu Asp Pro Glu
        530                535                540

Val Gln Phe Asn Trp Tyr Val Asp Gly Val Glu Val His Asn Ala Lys
545                550                555                560
```

```
Thr Lys Pro Arg Glu Glu Gln Phe Asn Ser Thr Tyr Arg Val Val Ser
            565                 570                 575

Val Leu Thr Val Leu His Gln Asp Trp Leu Asn Gly Lys Glu Tyr Lys
            580                 585                 590

Cys Lys Val Ser Asn Lys Gly Leu Pro Ser Ser Ile Glu Lys Thr Ile
            595                 600                 605

Ser Lys Ala Lys Gly Gln Pro Arg Glu Pro Gln Val Tyr Thr Leu Pro
    610                 615                 620

Pro Cys Gln Glu Glu Met Thr Lys Asn Gln Val Ser Leu Trp Cys Leu
625                 630                 635                 640

Val Lys Gly Phe Tyr Pro Ser Asp Ile Ala Val Glu Trp Glu Ser Asn
            645                 650                 655

Gly Gln Pro Glu Asn Asn Tyr Lys Thr Thr Pro Pro Val Leu Asp Ser
            660                 665                 670

Asp Gly Ser Phe Phe Leu Tyr Ser Arg Leu Thr Val Asp Lys Ser Arg
            675                 680                 685

Trp Gln Glu Gly Asn Val Phe Ser Cys Ser Val Met His Glu Ala Leu
    690                 695                 700

His Asn His Tyr Thr Gln Lys Ser Leu Ser Leu Ser Leu Gly
705                 710                 715

<210> SEQ ID NO 7
<211> LENGTH: 214
<212> TYPE: PRT
<213> ORGANISM: Artificial
<220> FEATURE:
<223> OTHER INFORMATION: CD20-binding moiety light chain

<400> SEQUENCE: 7

Glu Ile Val Leu Thr Gln Ser Pro Ala Thr Leu Ser Leu Ser Pro Gly
1                   5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
            85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205
```

```
Phe Asn Arg Gly Glu Cys
    210

<210> SEQ ID NO 8
<211> LENGTH: 448
<212> TYPE: PRT
<213> ORGANISM: Artificial
<220> FEATURE:
<223> OTHER INFORMATION: CD20-binding moiety heavy chain

<400> SEQUENCE: 8

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Cys Thr
            340                 345                 350
```

-continued

```
Leu Pro Pro Ser Gln Glu Glu Met Thr Lys Asn Gln Val Ser Leu Ser
        355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
        435                 440                 445

<210> SEQ ID NO 9
<211> LENGTH: 718
<212> TYPE: PRT
<213> ORGANISM: Artificial
<220> FEATURE:
<223> OTHER INFORMATION: CD3-binding moiety

<400> SEQUENCE: 9

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
                20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Gly Gly Ser Gly Gly Gly Gly Ser Gly
        210                 215                 220

Gly Gly Gly Ser Gly Gly Gly Gly Ser Gly Gly Gly Gly Ser Gly Gly
225                 230                 235                 240

Gly Gly Ser Gly Gly Gly Gly Ser Gly Gly Gly Gly Ser Gly Gly Gly
                245                 250                 255

Gly Ser Gly Gly Gly Gly Ser Gly Gly Gly Gly Ser Gly Gly Gly Gly
        260                 265                 270
```

-continued

```
Ser Asp Ile Lys Leu Gln Gln Ser Gly Ala Glu Leu Ala Arg Pro Gly
    275                 280                 285

Ala Ser Val Lys Met Ser Cys Lys Thr Ser Gly Tyr Thr Phe Thr Arg
    290                 295                 300

Tyr Thr Met His Trp Val Lys Gln Arg Pro Gly Gln Gly Leu Glu Trp
305                 310                 315                 320

Ile Gly Tyr Ile Asn Pro Ser Arg Gly Tyr Thr Asn Tyr Asn Gln Lys
                325                 330                 335

Phe Lys Asp Lys Ala Thr Leu Thr Thr Asp Lys Ser Ser Ser Thr Ala
                340                 345                 350

Tyr Met Gln Leu Ser Ser Leu Thr Ser Glu Asp Ser Ala Val Tyr Tyr
                355                 360                 365

Cys Ala Arg Tyr Tyr Asp Asp His Tyr Cys Leu Asp Tyr Trp Gly Gln
    370                 375                 380

Gly Thr Thr Leu Thr Val Ser Ser Ala Ser Thr Lys Gly Pro Ser Val
385                 390                 395                 400

Phe Pro Leu Ala Pro Cys Ser Arg Ser Thr Ser Glu Ser Thr Ala Ala
                405                 410                 415

Leu Gly Cys Leu Val Lys Asp Tyr Phe Pro Glu Pro Val Thr Val Ser
                420                 425                 430

Trp Asn Ser Gly Ala Leu Thr Ser Gly Val His Thr Phe Pro Ala Val
                435                 440                 445

Leu Gln Ser Ser Gly Leu Tyr Ser Leu Ser Ser Val Val Thr Val Pro
    450                 455                 460

Ser Ser Ser Leu Gly Thr Lys Thr Tyr Thr Cys Asn Val Asp His Lys
465                 470                 475                 480

Pro Ser Asn Thr Lys Val Asp Lys Arg Val Glu Ser Lys Tyr Gly Pro
                485                 490                 495

Pro Cys Pro Pro Cys Pro Ala Pro Glu Phe Leu Gly Gly Pro Ser Val
                500                 505                 510

Phe Leu Phe Pro Pro Lys Pro Lys Asp Thr Leu Met Ile Ser Arg Thr
                515                 520                 525

Pro Glu Val Thr Cys Val Val Val Asp Val Ser Gln Glu Asp Pro Glu
    530                 535                 540

Val Gln Phe Asn Trp Tyr Val Asp Gly Val Glu Val His Asn Ala Lys
545                 550                 555                 560

Thr Lys Pro Arg Glu Glu Gln Phe Asn Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Gly Leu Pro Ser Ser Ile Glu Lys Thr Ile
                595                 600                 605

Ser Lys Ala Lys Gly Gln Pro Arg Glu Pro Gln Val Tyr Thr Leu Pro
    610                 615                 620

Pro Cys Gln Glu Glu Met Thr Lys Asn Gln Val Ser Leu Trp Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Arg Leu Thr Val Asp Lys Ser Arg
                675                 680                 685
```

```
Trp Gln Glu Gly Asn Val Phe Ser Cys Ser Val Met His Glu Ala Leu
    690             695             700

His Asn His Tyr Thr Gln Lys Ser Leu Ser Leu Ser Leu Gly
705             710             715
```

```
<210> SEQ ID NO 10
<211> LENGTH: 722
<212> TYPE: PRT
<213> ORGANISM: Artificial
<220> FEATURE:
<223> OTHER INFORMATION: CD20-binding moiety

<400> SEQUENCE: 10
```

```
Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
                20              25              30

Leu Ala Trp Tyr Gln Gln Lys Pro Gly Gln Ala Pro Arg Leu Leu Ile
            35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Pro Ile
                85              90              95

Thr Phe Gly Gln Gly Thr Arg Leu Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys Gly Gly Gly Gly Ser Gly Gly Gly Gly Ser
    210             215             220

Gly Gly Gly Gly Ser Gly Gly Gly Ser Gly Gly Gly Gly Ser Gly
225             230             235             240

Gly Gly Gly Ser Gly Gly Gly Ser Gly Gly Gly Gly Ser Gly Gly
            245             250             255

Gly Gly Ser Gly Gly Gly Gly Ser Gly Gly Gly Gly Ser Gly Gly Gly
            260             265             270

Gly Ser Glu Val Gln Leu Val Glu Ser Gly Gly Gly Leu Val Gln Pro
            275             280             285

Gly Arg Ser Leu Arg Leu Ser Cys Ala Ala Ser Gly Phe Thr Phe Asn
    290             295             300

Asp Tyr Ala Met His Trp Val Arg Gln Ala Pro Gly Lys Gly Leu Glu
305             310             315             320

Trp Val Ser Thr Ile Ser Trp Asn Ser Gly Ser Ile Gly Tyr Ala Asp
            325             330             335
```

-continued

```
Ser Val Lys Gly Arg Phe Thr Ile Ser Arg Asp Asn Ala Lys Lys Ser
            340                 345                 350

Leu Tyr Leu Gln Met Asn Ser Leu Arg Ala Glu Asp Thr Ala Leu Tyr
            355                 360                 365

Tyr Cys Ala Lys Asp Ile Gln Tyr Gly Asn Tyr Tyr Tyr Gly Met Asp
        370                 375                 380

Val Trp Gly Gln Gly Thr Thr Val Thr Val Ser Ser Ala Ser Thr Lys
385                 390                 395                 400

Gly Pro Ser Val Phe Pro Leu Ala Pro Cys Ser Arg Ser Thr Ser Glu
                405                 410                 415

Ser Thr Ala Ala Leu Gly Cys Leu Val Lys Asp Tyr Phe Pro Glu Pro
                420                 425                 430

Val Thr Val Ser Trp Asn Ser Gly Ala Leu Thr Ser Gly Val His Thr
            435                 440                 445

Phe Pro Ala Val Leu Gln Ser Ser Gly Leu Tyr Ser Leu Ser Ser Val
        450                 455                 460

Val Thr Val Pro Ser Ser Ser Leu Gly Thr Lys Thr Tyr Thr Cys Asn
465                 470                 475                 480

Val Asp His Lys Pro Ser Asn Thr Lys Val Asp Lys Arg Val Glu Ser
                485                 490                 495

Lys Tyr Gly Pro Pro Cys Pro Pro Cys Pro Ala Pro Glu Phe Leu Gly
            500                 505                 510

Gly Pro Ser Val Phe Leu Phe Pro Pro Lys Pro Lys Asp Thr Leu Met
            515                 520                 525

Ile Ser Arg Thr Pro Glu Val Thr Cys Val Val Val Asp Val Ser Gln
        530                 535                 540

Glu Asp Pro Glu Val Gln Phe Asn Trp Tyr Val Asp Gly Val Glu Val
545                 550                 555                 560

His Asn Ala Lys Thr Lys Pro Arg Glu Glu Gln Phe Asn Ser Thr Tyr
                565                 570                 575

Arg Val Val Ser Val Leu Thr Val Leu His Gln Asp Trp Leu Asn Gly
            580                 585                 590

Lys Glu Tyr Lys Cys Lys Val Ser Asn Lys Gly Leu Pro Ser Ser Ile
            595                 600                 605

Glu Lys Thr Ile Ser Lys Ala Lys Gly Gln Pro Arg Glu Pro Gln Val
        610                 615                 620

Cys Thr Leu Pro Pro Ser Gln Glu Glu Met Thr Lys Asn Gln Val Ser
625                 630                 635                 640

Leu Ser Cys Ala Val Lys Gly Phe Tyr Pro Ser Asp Ile Ala Val Glu
                645                 650                 655

Trp Glu Ser Asn Gly Gln Pro Glu Asn Asn Tyr Lys Thr Thr Pro Pro
            660                 665                 670

Val Leu Asp Ser Asp Gly Ser Phe Phe Leu Val Ser Arg Leu Thr Val
            675                 680                 685

Asp Lys Ser Arg Trp Gln Glu Gly Asn Val Phe Ser Cys Ser Val Met
        690                 695                 700

His Glu Ala Leu His Asn His Tyr Thr Gln Lys Ser Leu Ser Leu Ser
705                 710                 715                 720

Leu Gly
```

<210> SEQ ID NO 11
<211> LENGTH: 5
<212> TYPE: PRT
<213> ORGANISM: Artificial

-continued

```
<220> FEATURE:
<223> OTHER INFORMATION: tandemly repeated sequence

<400> SEQUENCE: 11

Gly Gly Gly Gly Ser
1               5
```

BISPECIFIC ANTIBODY TARGETING CD3 AND CD20 AND USE THEREOF

RELATED APPLICATION

This application is a U.S. National Phase application of International Patent Application No. PCT/CN2020/103731, filed Jul. 23, 2020, which claims priority to Chinese application No. 201910764107.6, filed Aug. 19, 2019; the disclosure of which are herein incorporated by reference in its entirety.

FIELD OF THE INVENTION

The present invention relates to an anti-CD3 single chain Fab molecule and an anti-CD20 single chain Fab molecule, and also to a bispecific antibody targeting CD3 and CD20 and use thereof.

BACKGROUND OF THE INVENTION

B-cell lymphoma is a common hematologic disorder classified as Hodgkin's lymphoma and non-Hodgkin's lymphoma. Its etiology is unknown, and immunodeficiency and environmental factors are considered as possible factors in its development. The treatment and prognosis of B-cell lymphoma depends on the specific type of lymphoma and the stage classification. Depending on the clinical progression, B-cell lymphoma is classified as inert lymphomas and aggressive lymphomas. Inert lymphomas usually progress slowly and maintain stable and long-term survival for many years, but are not curable, while aggressive lymphomas usually require immediate and urgent treatment. The current treatment of B-lymphocytoma is not satisfactory due to the lack of effective therapeutic drugs.

CD3 is a differentiation antigen expressed only on the surface of T cells linked to the T cell receptor (TCR) and is a molecule necessary for T cell activation. CD3 includes four chains, ε, ζ, δ and γ, while functional CD3 is a dimer formed by two of these chains. An anti-CD3 antibody can bind to CD3 on the surface of T cells, producing effects similar to those of the TCR-CD3 molecule and thus activating T lymphocytes.

CD20 is a B-cell marker expressed in mature and activated B-lymphocytes and is widely expressed in B-cell non-Hodgkin's lymphoma and other B-cell malignancies, but not in cells such as precursor B-lymphocytes, plasma cells and lymphoid pluripotent stem cells. In addition, CD20 antigen is clearly revealed and easily identified, and no free CD20 is present in serum in the body. Therefore, CD20 is a good therapeutic target for B-lymphocytoma.

Since CD3 and CD20 are specific targets for T and B lymphocytes with good drug-forming potential, several research teams have constructed or are constructing bispecific antibodies targeting CD3 and CD20, and some have applied for patents (e.g. CN104640881A and CN104558191A), but due to the limitations of molecular structure and development technology, bispecific antibodies usually suffer from low expression, heavy chain mismatch, decreased binding of antibody and antigen, and cumbersome purification processes.

SUMMARY OF THE INVENTION

In an aspect, the present invention provides an anti-CD3 single chain Fab molecule comprising a Fab light chain and a Fab heavy chain, wherein C-terminal of the Fab light chain is connected to N-terminal of the Fab heavy chain by a linking peptide having a length of 45 to 80 amino acids.

In some embodiments, the linking peptide has a length of 60 amino acids.

In some embodiments, the linking peptide comprises a tandemly repeated GGGGS (SEQ ID NO: 11) sequence.

In some embodiments, the anti-CD3 single chain Fab molecule comprises an amino acid sequence having at least 90% identity to the sequence as set forth in SEQ ID NO: 6 or 9.

In another aspect, the present invention provides an anti-CD20 single chain Fab molecule comprising a Fab light chain and a Fab heavy chain, wherein C-terminal of the Fab light chain is connected to N-terminal of the Fab heavy chain by a linking peptide having a length of 45 to 80 amino acids.

In some embodiments, the linking peptide has a length of 60 amino acids.

In some embodiments, the linking peptide comprises a tandemly repeated GGGGS sequence.

In some embodiments, the anti-CD20 single chain Fab molecule comprises an amino acid sequence having at least 90% identity to the sequence as set forth in SEQ ID NO: 10.

In another aspect, the present invention provides use of the anti-CD3 single chain Fab molecule or the anti-CD20 single chain Fab molecule for preparation of a bispecific antibody.

In another aspect, the present invention provides a bispecific antibody comprising a first moiety for binding to CD3 and a second moiety for binding to CD20, wherein the first moiety is an anti-CD3 single chain Fab molecule comprising a Fab light chain and a Fab heavy chain with C-terminal of the Fab light chain being connected to the N-terminal of the Fab heavy chain by a linking peptide having a length of 45 to 80 amino acids; the second moiety comprises a light chain and a heavy chain of an anti-CD20 antibody.

In some embodiments, the linking peptide has a length of 60 amino acids.

In some embodiments, the linking peptide comprises a tandemly repeated GGGGS sequence.

In some embodiments, the first moiety for binding to CD3 comprises an amino acid sequence having at least 90% identity to the sequence as set forth in SEQ ID NO: 6 or 9.

In some embodiments, the light chain of the anti-CD20 antibody comprises an amino acid sequence having at least 90% identity to the sequence as set forth in SEQ ID NO: 7, and the heavy chain of the anti-CD20 antibody comprises an amino acid sequence having at least 90% identity to the sequence as set forth in SEQ ID NO: 8.

In some embodiments, C-terminal of the light chain of the anti-CD20 antibody is linked to N-terminal of the heavy chain of the anti-CD20 antibody by a linking peptide.

In some embodiments, the second moiety for binding to CD20 comprises an amino acid sequence having at least 90% identity to the sequence as set forth in SEQ ID NO: 10.

In another aspect, the present invention provides use of the bispecific antibody in preparation of a medicament for treatment of a B-cell related disease.

In some embodiments, the B-cell related disease is B-cell leukemia or B-cell lymphoma.

In another aspect, the present invention provides a pharmaceutical composition comprising the bispecific antibody and a pharmaceutically acceptable carrier.

In another aspect, the present invention provides a method of treating a B-cell related disease in a patient comprising administering to the patient a therapeutically effective amount of the bispecific antibody or the pharmaceutical composition.

DETAILED DESCRIPTION OF THE INVENTION

Figure 1:
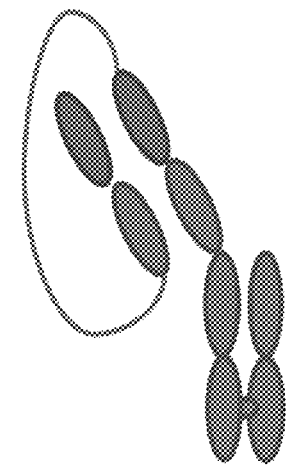
FIG. 1 shows a schematic structure of the candidate molecule prepared in Example 1 for assessing the effect of the linking peptide on the properties of the single-chain Fab molecule.

Unless otherwise indicated, all technical and scientific terms used herein have the meanings commonly understood by those of ordinary skill in the art.

"Antibodies" are immunoglobulins secreted by plasma cells (effector B cells) and used by the body's immune system to neutralize foreign substances (peptides, viruses, bacteria, etc.). The foreign substance is accordingly called an antigen. The basic structure of a classical antibody molecule is a tetramer consisting of two identical heavy chains and two identical light chains. The heavy chain is divided into a variable region located at the amino terminus (VH) and a constant region located at the carboxyl terminus (CH) based on the difference in conserved amino acid sequences. The light chain is similarly divided into a variable region (VL) located at the amino terminus and a constant region (CL) located at the carboxyl terminus. The variable region of a heavy chain and a light chain interact to form the antigen binding site (Fv). The constant region of the light chain includes only one Ig domain, while the constant region of the heavy chain includes different numbers of Ig domains depending on the type of antibody (Isotype). For example, IgG, IgA, and IgD include three Ig domains: CH1, CH2, and CH3, while IgM and IgE include four Ig domains: CH1, CH2, CH3, and CH4.

"Fab" refers to the fragment of antigen binding, which consists of an intact light chain of the antibody and the VH and CH1 structural domains of the heavy chain. In some embodiments of the present invention, the C-terminal of the light chain of Fab is linked to the N-terminal of the heavy chain by a short linking peptide to form a "single chain Fab (scFab) molecule". For the convenience of description, the light chain portion of the single chain Fab molecule is referred to as the "Fab light chain" and the heavy chain portion is referred to as the "Fab heavy chain" in some contexts where Fab is mentioned. In some embodiments, the Fab heavy chain may also include an Fc fragment attached at the C-terminal.

The "linking peptide", which is described in more detail herein in examples, may have a length of 40 to 80 (e.g., 50, 52, 55, 58, 60, 62, 65, 70, 75, or 78) amino acids. Use of linking peptides helps stabilize the molecular structure and prevent light chain mismatches in bispecific antibodies.

The "Fc fragment" is a fragment crystallizable region, which corresponds to the CH2 and CH3 structural domains of IgG antibody. IgG can bind to cells with corresponding receptors on their surface through its Fc fragment to produce different biological effects, such as opsonization and antibody-dependent cell-mediated cytotoxic effects (ADCC). The antibody Fc fragment can be obtained by hydrolysis of the antibody molecule by protein hydrolases (e.g. papain). In some embodiments, the "Fc fragment" may also comprise a hinge region of the antibody heavy chain. In some embodiments, the "Fc fragment" is derived from IgG, IgA, IgD, or IgM antibodies.

In some embodiments, a single-chain Fab molecule for binding CD3 acts as a CD3-binding moiety to bind to another antigen-binding moiety to form a bispecific antibody targeting CD3 and that other antigen. In some embodiments, the single-chain Fab molecule acts as a CD3-binding moiety to bind to a CD20-binding moiety to form a bispecific antibody targeting CD3 and CD20. In some embodiments, the single-chain Fab molecule acts as a CD3-binding moiety to bind to a variety of additional antigen-binding moieties to form a multispecific antibodies.

In some embodiments, a single-chain Fab molecule for binding CD20 acts as a CD20-binding moiety to bind to another antigen-binding moiety to form a bispecific antibody targeting CD20 and that other antigen. In some embodiments, the single-chain Fab molecule acts as a CD20-binding moiety to bind to a CD3-binding moiety to form a bispecific antibody targeting CD3 and CD20. In some embodiments, the single-chain Fab molecule acts as a CD20-binding moiety to bind to a variety of additional antigen-binding moieties to form multispecific antibodies.

The binding of the CD20-binding moiety to the CD3-binding moiety of the bispecific antibody of the present invention may be covalent (e.g., through the formation of disulfide bonds between Fc fragments) or non-covalent.

In some embodiments, the light and heavy chain variable structural domains of the CD3-binding moiety of the bispecific antibody are derived from OKT3 monoclonal antibody or L2K monoclonal antibody (WO2004106380). In some embodiments, the light and heavy chain variable structural domains of the CD20-binding moiety of the bispecific antibody are derived from Rituximab or Ofatumumab.

When it is referred that an antibody "binds" to an antigen, it means that the antibody is capable of recognizing and detectably binding to that antigen. The binding of an antibody to an antigen can be determined by a well-known antigen-antibody binding assay, such as an ELISA. In addition, the dissociation equilibrium constant for antibody-antigen binding, KD, can be used to express the binding affinity of the antibody to the corresponding antigen.

In some embodiments of the present invention, the "Knobs-into-holes" structure of the Fc fragment is used to prevent heavy chain mismatches in bispecific antibodies. This technology was developed by Genentech (see U.S. Pat. No. 5,731,168), which is done by mutating a threonine (T) with a smaller volume at position 366 in the heavy chain CH3 region of one of the antibodies to a tyrosine (Y) with a larger volume, forming a prominent "knob" structure (T366Y, (Kabat numbering system)); while mutating a tyrosine (Y) with a larger volume at position 407 in the heavy chain CH3 region of the other antibody to a tyrosine (T) with small volume, forming a concave "hole" structure (Y407T). The correct assembly between two different antibody heavy chains is achieved by exploiting the spatial site blocking effect of the "Knobs-into-holes" structure. After the mutation, the product correct assembly rate has improved significantly and can meet the requirements of large-scale production. However, the modification of the heavy chain CH3 reduces the stability of the antibody structure. To overcome the drawback, a more stable "3+1" pattern is constructed by random mutation screening through phage display technique, i.e., the T366W mutation formed a prominent "knob" type and three amino acid mutations (T366S, L368A and Y407V) formed a concave "hole" type. The Knobs-holes structure is designed to facilitate the assembly of two heterologous antibody heavy chains.

"Sequence identity" refers to the degree of similarity between amino acid or nucleotide sequences and is generally expressed as a percentage of identity, which can be determined by visual inspection or by computer programs (e.g. BLAST). In some embodiments of the present invention, the single-stranded Fab molecule for binding to CD3 comprises the amino acid sequence as set forth in SEQ ID NO: 6, or comprises an amino acid sequence having at least 80% (e.g., at least 90%, at least 95%, at least 98%, or at least 99% or 100%) sequence identity to the sequence as set forth in SEQ ID NO: 6.

In some embodiments of the present invention, the CD3-binding moiety of the bispecific antibody comprises the amino acid sequence as set forth in SEQ ID NO: 6 or comprises an amino acid sequence having at least 80% (e.g., at least 90%, at least 95%, at least 98%, at least 99%, or 100%) sequence identity to the sequence as set forth in SEQ ID NO: 6. In some embodiments of the present invention, the light chain of the CD20-binding moiety of the bispecific antibody comprises the amino acid sequence as set forth in SEQ ID NO: 7, or comprises an amino acid sequence having at least 80% (e.g., at least 90%, at least 95%, at least 98%, at least 99%, or 100%) sequence identity with the sequence as set forth in SEQ ID NO: 7; the heavy chain of the CD20-binding moiety of the bispecific antibody comprises the amino acid sequence as set forth in SEQ ID NO: 8, or comprises an amino acid sequence having at least 80% (e.g., at least 90%, at least 95%, at least 98%, at least 99%, or 100%) sequence identity to the sequence as set forth in SEQ ID NO: 8.

In some embodiments of the present invention, the CD3-binding moiety of the bispecific antibody comprises the amino acid sequence as set forth in SEQ ID NO: 9 or comprises an amino acid sequence having at least 80% (e.g., at least 90%, at least 95%, at least 98%, at least 99%, or 100%) sequence identity to the sequence as set forth in SEQ ID NO: 9. In some embodiments of the present invention, the CD20-binding moiety of the bispecific antibody comprises the amino acid sequence as set forth in SEQ ID NO: 10 or comprises an amino acid sequence having at least 80% (e.g., at least 90%, at least 95%, at least 98%, at least 99%, or 100%) sequence identity to the sequence as set forth in SEQ ID NO: 10.

It will be understood by those skilled in the art that, on the basis of the specific sequences provided herein, the corresponding variants of the single-chain Fab molecules or bispecific antibodies for binding to CD3 or CD20 provided herein can be obtained by substituting, deleting, or adding a plurality of amino acids and verifying or screening the binding capacity or biological activity of the resulting products with the corresponding antigens, which shall also be included in the scope of the present invention.

When referring to pharmaceutical compositions, the term "pharmaceutically acceptable carrier" is used to refer to a solid or liquid diluent, filler, antioxidant, stabilizer, etc., that can be safely administered and is suitable for human and/or animal administration without undue adverse side effects and is suitable for maintaining the viability of the drug or active agent located therein.

The term "therapeutically effective amount" means an amount of an active compound that is sufficient to elicit a biological or medical response in a subject as desired by the clinician. An "therapeutically effective amount" of the bispecific antibody of the present invention can be determined by those skilled in the art based on route of administration, weight, age, and condition, etc. of the subject. For example, a typical daily dose can range from 0.01 mg to 100 mg of active ingredient per kg of body weight.

The present invention is further described below in combination with specific examples.

Example 1. Screening of Lengths of Flexible Linking Peptides Used to Construct the Anti-CD3 Single Chain Fab Molecules Based on the spatial structure of the Fab molecule, the inventors designed a single-chain Fab molecule targeting CD3, i.e., the light chain and its corresponding heavy chain variable region, as well as the CH1 fragment and the "knob" Fc fragment, were linked by a flexible linking peptide, in which the light chain and heavy chain variable region sequences were derived from the L2K antibody. The resulting single chain Fab molecule had the amino acid sequence as set forth in SEQ ID NO: 6.

Considering that the length of the flexible linking peptide should be not less than 3.5 nm and the distance between adjacent peptide bonds of amino acids is 0.38 nm, and considering that the spatial structure of scFab needs to maintain a certain flexibility, we designed several flexible linking peptides with lengths between 26 and 80 amino acids, and the lengths and sequences of five representative linking peptides are shown in Table 1.

TABLE 1

| | Number of amino | |
|---|---|---|
| SEQ ID NO | acids of flexibly linking peptides | Amino acid sequences of flexibly linking peptides |
| 1 | 26 | GGGSGGSGGSGGSGGSGGSGGSGGSG |
| 2 | 32 | GGGGSGGGGSGGGGSGGGGSGGGGSGGGGSGG |
| 3 | 45 | GGGGSGGGGSGGGGSGGGGSGGGGSGGGGSGGGGSGGGGSGGGGS |
| 4 | 60 | GGGGSGGGGSGGGGSGGGGSGGGGSGGGGSGGGGSGGGGSGGGGSGGGGSGGGGSGGGGS |
| 5 | 80 | GGGGSGGGGSGGGGSGGGGSGGGGSGGGGSGGGGSGGGGSGGGGSGGGGSGGGGSGGGGSGGGGSGGGGSGGGGSGGGGS |

1.1 Effect of Different Lengths of Flexible Linking Peptides on Expression Levels The nucleic acid sequences encoding the above single-stranded Fab molecules and the "hole" Fc fragment were synthesized by overlapping PCR techniques and cloned into the eukaryotic expression vector pcDNA (purchased from Life Technologies, Inc.), respectively. Then, the DNA-transfection reagent complex was prepared by mixing the expression vector including the nucleic acid sequence encoding the single-stranded Fab molecule and the expression vector including the sequence encoding the "hole" Fc fragment at a ratio of 1.5:1 to a mixture of 200 µg in total, and then mixing with the transfection reagent PEI (polyethylenimine) at a mass to volume ratio of 1:2.5. The DNA-transfection reagent complex was added dropwise to 200 mL of 293F cells in logarithmic growth phase. The cell supernatant was collected 5-7 days after transfection, filtered through a 0.45 µm membrane, and added to an affinity chromatography gel column (Protein A) rinsed with binding buffer (12.15 g of Tris (Tris(hydroxymethyl)aminomethane) dissolved in sterilized water, pH adjusted to 7.0, 8.78 g of NaCl added, and volume balanced to 1 L), followed by elution solution (7.5 g glycine dissolved in double-distilled water, pH 3.5, 8.78 g NaCl, volume balanced to 1 L). The column was then eluted with eluent (7.5 g of glycine dissolved in double-distilled water, pH adjusted to 3.5, 8.78 g of NaCl added, and volume balanced to 1 L). The elution fraction was neutralized with 1 M Tris-HCl (Tris(hydroxymethyl)aminomethane-HCl), pH 9.0 to obtain candidate molecules with different lengths of flexible linking peptide linkages (structures are shown schematically in FIG. 1).

Figure 2:
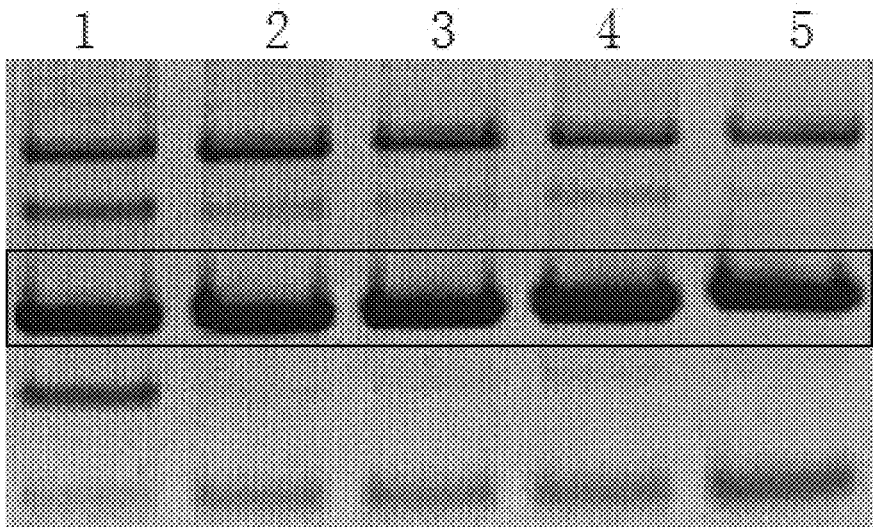
FIG. 2 shows the results of SDS-PAGE electrophoresis analysis of the above candidate molecules with different length linking peptides expressed in cells and purified.

After taking 20 µL of eluate and adding the sample loading buffer, the protein was denatured at 95° C. for 10 minutes and separated by polyacrylamide gel electrophoresis, and the bands were shown by Coomassie Brilliant Blue staining. The staining results are shown in FIG. 2. Lanes 1 to 5 correspond to candidate molecules comprising flexible linking peptides of 26, 32, 45, 60 and 80 amino acids in length, respectively. As seen in the figure, the candidate molecule constructed using the flexible linking peptide of 60 amino acids in length (the bands marked by black boxes in the figure, Fab single chain molecule containing the Fc fragment) had slightly higher expression and fewer impurity bands.

1.2 Effect of Different Lengths of Flexible Linking Peptides on Thermal Stability The purified proteins (candidate molecules) from part 1.1 above were subjected to heat treatment at 37° C. for 24 hours and 50° C. for 2 hours, respectively, and were subjected to SEC-HPLC along with the antibodies placed at 4° C. for the same treatment time. The operation of SEC-HPLC detection is briefly described as follows: TSKgel® G3000SWXL gel column (TOSOH Corporation) was selected and the column was equilibrated with the mobile phase (50 mM phosphate buffer, 150 mM NaCl, pH 7.0) followed by UV detection. 50 µL of each protein treated at different temperatures was passed through the column at a flow rate of 1 mL/min, and each sample was run for 20 minutes to fit the result graph and calculate the purity of the target protein.

The results are shown in Table 2. Overall, as the length of the flexible linking peptide increased, the thermal stability of the antibody also became better, i.e., the difference with the protein in a state at 4° C. was smaller. The candidate molecule constructed with the flexible linking peptide of 60 amino acids in length exhibited the best thermal stability when treated at 50° C.

TABLE 2

Comparison of thermal stability of candidate molecules constructed by flexible linking peptides of different lengths

| Number of amino acids of flexibly linking peptides | Difference in purity between 37° C. and 4° C. heat treatment (%) | Difference in purity between 50° C. and 4° C. heat treatment (%) |
|---|---|---|
| 26 | 2.95 | 8.21 |
| 32 | 2.62 | 4.87 |
| 45 | 1.94 | 3.52 |
| 60 | 1.78 | 2.90 |
| 80 | 0.83 | 3.19 |

1.3 Effect of Different Lengths of Flexible Linking Peptides on Antigen Binding Ability The binding ability of the purified antibodies (i.e., candidate molecules) in part 1.1 above to CD3 antigen was measured by ELISA. The brief procedure was as follows: 100 µL of CD3 antigen (Sino Biologics, SEK10981) at a concentration of 0.5 µg/mL was coated on an ELISA plate and placed at 4° C. overnight. After washing with PBS buffer containing 2% BSA, the plates were washed three times using PBS containing 2% BSA after blocked at room temperature for 1 hour. Then, 100 µL of antibody containing the gradient dilution was added and incubated for 1 hour at room temperature followed by 3 washes, and 100 µL of horseradish peroxidase-labeled sheep anti-human IgG secondary antibody (Bethyl Laboratories, Inc., 1:5000 dilution)

was added and incubated for 1 hour at room temperature. After 3 washes, 100 μL of TMB chromogenic solution was added to develop the color, and the absorbance value at 450 nm was read on an enzyme marker.

Figure 3:
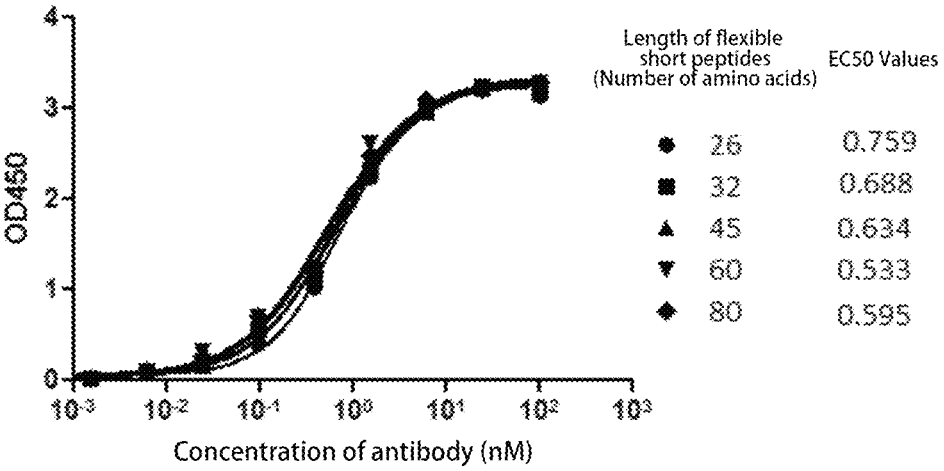
FIG. 3 shows the results of the assay of CD3 binding ability of the above candidate molecules with different lengths of linking peptides.

The results are shown in FIG. 3. Broadly speaking, as the length of the flexible linking peptide increased, the EC50 value decreased, i.e., the binding capacity increased. Among them, the candidate molecule constructed with the flexible linking peptide of 60 amino acids in length exhibited the best antigen binding ability (smallest EC50 value).

Comprehensively considering the effects of different lengths of flexible linking peptides on the expression level, thermal stability and antigen binding ability, we chose the flexible linking peptide of 60 amino acids in length for the subsequent construction of bispecific antibodies.

Example 2. Preparation of Bispecific Antibodies

Figure 4:
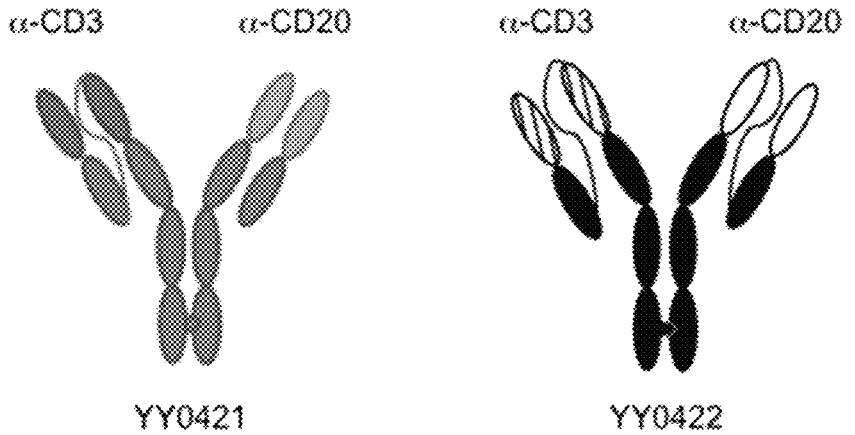
FIG. 4 shows the structure of the bispecific antibodies YY0421 and YY0422 of the present invention. α-CD3 refers to the CD3-binding moiety and α-CD20 refers to the CD20-binding moiety.

The DNA fragment encoding the CD3-binding moiety (anti-CD3 single chain Fab molecule, amino acid sequence SEQ ID NO: 6) and the DNA fragments encoding the anti-CD20 antibody light chain and heavy chain (amino acid sequences SEQ ID NO: 7 and SEQ ID NO: 8, respectively) were synthesized and cloned into eukaryotic expression vector pcDNA (purchased from Life Technologies, Inc.) using recombinant DNA such as overlapping PCR techniques, and then the obtained expression vector containing the DNA sequence encoding the CD3-binding moiety, the expression vector containing the DNA sequence encoding the light chain of anti-CD20 antibody and the expression vector containing the DNA sequence encoding the heavy chain of anti-CD20 antibody were mixed in a mass ratio of 1.5:2:1. The DNA-transfection reagent complex was prepared by mixing 200 μg of the above expression vector mixture with transfection reagent PEI (polyethylenimine) at a mass to volume ratio of 1:2.5, and added dropwise to 200 mL of 293F cells in logarithmic growth phase. The cell supernatant was collected 5-7 days after transfection, filtered through a 0.45 μm membrane, and then the supernatant was added to an affinity chromatography gel column (Protein A) washed with binding buffer (12.15 g of Tris (Tris(hydroxymethyl)aminomethane) dissolved in appropriate amount of sterilized water, pH adjusted to 7.0, 8.78 g of NaCl added, volume balanced to 1 L), and then eluted with eluent (7.5 g of glycine dissolved in appropriate amount of double-distilled water, pH adjusted to 3.5, 8.78 g of NaCl added, volume balanced to 1 L). The elution fraction was neutralized with IM Tris-HCl (Tris(hydroxymethyl)aminomethane-HCl) pH 9.0 to obtain the bispecific antibody of the present invention YY0421. In a similar manner, the bispecific antibody of the present invention YY0422 was prepared, wherein the light and heavy chains of the CD20-binding moiety were linked by a linking peptide (the amino acid sequence of the CD3-binding moiety is shown in SEQ ID NO: 9, and the amino acid sequence of the CD20-binding moiety is shown in SEQ ID NO: 10). Schematic structures of the bispecific antibodies YY0421 and YY0422 are shown in FIG. 4.

Example 3 Western Blotting Assay 3.1 Assay for Ability of the Bispecific Antibody of the Present Invention to Recognize CD3

Jurkat cells with healthy cell morphology and 80% fusion rate were collected, centrifuged and the supernatant discarded. Cell lysate was added, denatured at 95° C. for 10 minutes, and then cell proteins were separated by polyacrylamide gel electrophoresis. The proteins were transferred to nitrocellulose membranes (NC membranes) using the semi-dry transfer method and blocked with 5% skim milk for 1 hour at room temperature. Antibodies YY0421, YY0422 of the present invention or control antibody REGN1979 (a CD3 and CD20 bispecific antibody, see WO2014047231 and US20170355767) were added, incubated for 1 hour at room temperature, washed with PBST, and then a horseradish peroxidase labelled secondary antibody was added and incubated for 1 hour at room temperature. After PBST washing, the color was developed using chemiluminescent reagent and developed in the dark room.

Figure 5:
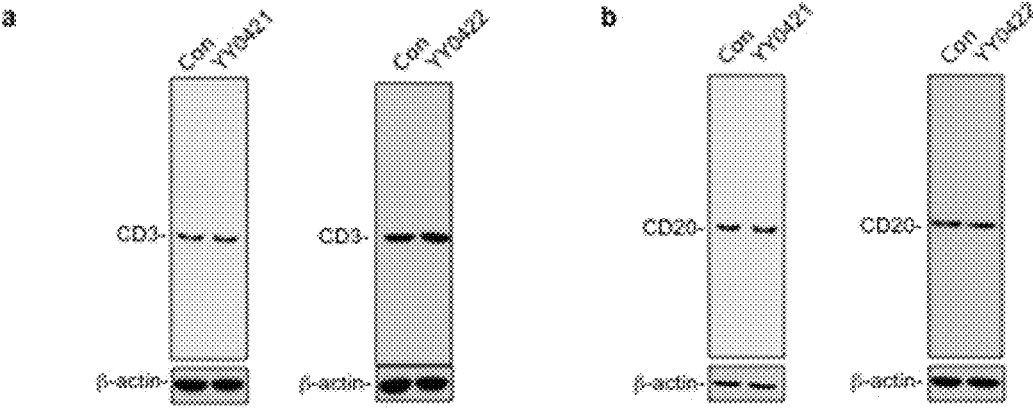
FIG. 5 shows the results of Western blotting assays of the bispecific antibody of the present invention and the bispecific antibody REGN1979 as a control (Con in the Figure) bound to CD3 (FIG. 5a) and CD20 (FIG. 5b).

The results of the Western blotting assay are shown in FIG. 5a. The results indicate that the bispecific antibodies YY0421 and YY0422, which target both human CD3 and CD20, can effectively recognize the CD3 antigen at the protein level.

3.2 Assay for Ability of the Bispecific Antibody of the Present Invention to Recognize CD20

Raji cells with healthy cell morphology and 80% fusion rate were collected, centrifuged and the supernatant was discarded. Cell lysate was added, denatured at 95° C. for 10 minutes, and then cell proteins were separated by polyacrylamide gel electrophoresis. The proteins were transferred to nitrocellulose membranes (NC membranes) using the semi-dry transfer method and blocked with 5% skim milk for 1 hour at room temperature. Antibodies YY0421, YY0422 of the present invention or control antibody REGN1979 were added, incubated for 1 hour at room temperature, washed with PBST, and then a horseradish peroxidase labelled secondary antibody was added and incubated for 1 hour at room temperature. After PBST washing, the color was developed using chemiluminescent reagent and developed in the dark room.

The results of the Western blotting assay are shown in FIG. 5b. The results indicate that the bispecific antibodies YY0421 and YY0422, which target both human CD3 and CD20, can effectively recognize the CD20 antigen at the protein level.

Example 4. Flow Cytometry for Detecting the Binding of Bispecific Antibodies of the Present Invention to CD3 and CD20 on Cell Surface Human Raji and Jurkat cells were inoculated in 6-well plates, incubated for 20 hours and then digested by trypsin (without EDTA) and collected, centrifuged at 1000 rpm for 5 minutes at room temperature and washed twice with PBS and incubated with YY0421, YY0422 or control antibody REGN1979 for 1 hour on ice, washed with PBS and incubated with FITC-labeled rabbit anti-human IgG (Fab) for 1 hour on ice and detected by flow cytometry.

Figure 6:
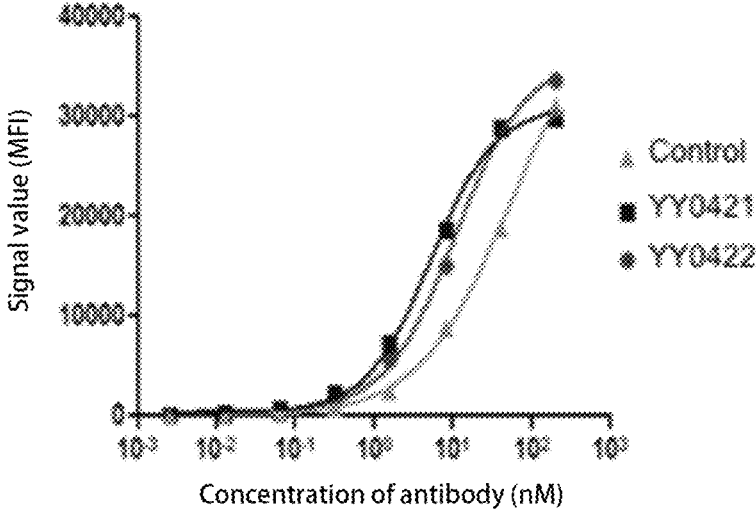
FIG. 6 shows the results of the assay for binding abilities of the bispecific antibody of the present invention and the bispecific antibody REGN1979 as a control to Raji cells.
Figure 7:
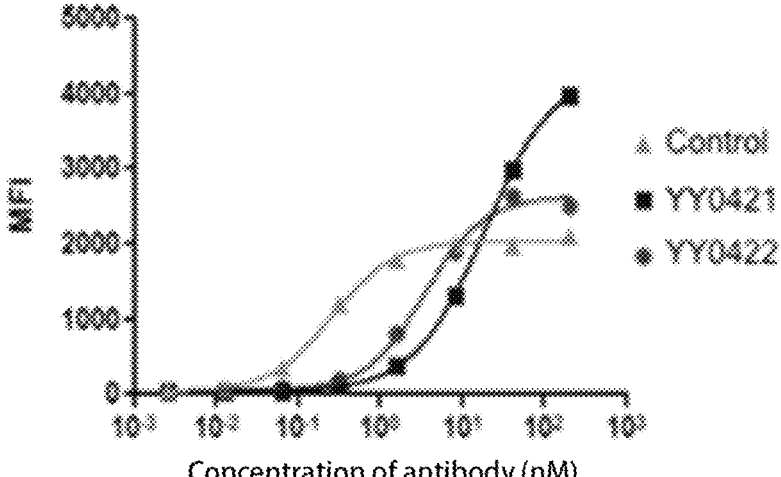
FIG. 7 shows the results of the assay for binding ability of the bispecific antibody of the present invention and the bispecific antibody REGN1979 as a control to Jurkat cells.

The results of the flow cytometry assay are shown in FIGS. 6 and 7. The results indicate that the bispecific antibodies YY0421 and YY0422 of the present invention, which target both human CD3 and CD20, had a high affinity for human CD3 (FIG. 6) and CD20 (FIG. 7) on the cell surface.

Example 6. Bispecific Antibodies of the Present Invention Mediate Killing of Tumor Cells by CD8 T Cells Morphologically healthy human Daudi cells in an amount of 5×10³, which were stained with CFSE of a final concentration of 5 μM, were inoculated in a 96-well plate. After overnight starvation with medium containing 0.5% fetal bovine serum, CD8 T cells were added at an E/T ratio of 5:1. The experiments were performed in two batches, each batch dividing the cells into three groups (each group comprised three wells). In the first batch, culture medium (Blank in FIG. 8a), control antibody REGN1979 (Control in FIG. 8a), and antibody YY0421 of the invention were added separately. In the second batch, culture medium (Blank in FIG. 8b), control antibody REGN1979 (Control in FIG. 8b), and antibody YY0422 of the present invention were added separately. Then, the incubation was continued in the cell incubator for 4 hours. The supernatant and cell suspension were collected, centrifuged, with supernatant discarded and then resuspended with PBS, followed by the addition of 1 μg/mL PI, and the ratio of CFSE and PI double-positive cells to CFSE-positive cells was detected by flow cytometry to detect the ability of bispecific antibodies to mediate CD8 T killing of tumor cells.

Figure 8:
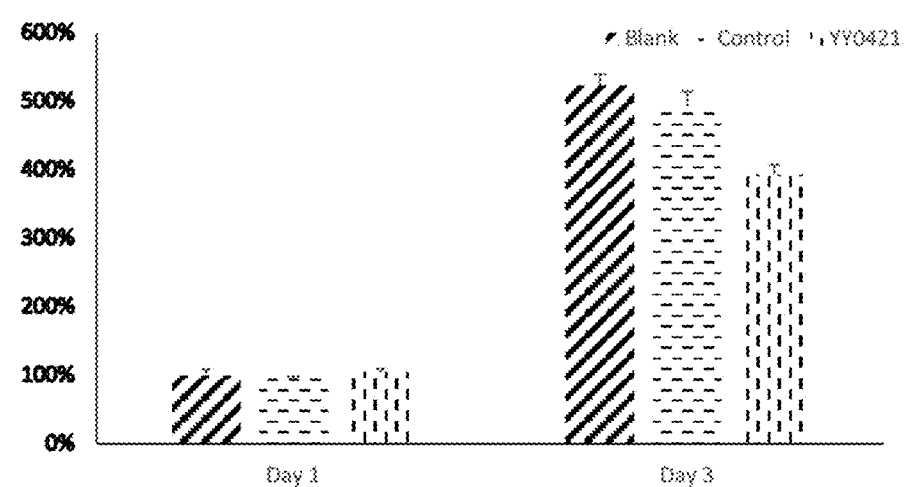
FIG. 8 shows the results of killing of human Daudi cells (FIG. 8) by the bispecific antibody of the present invention and the bispecific antibody REGN1979 as a control. The vertical coordinate indicates the value of relative change in proliferation.
Figure 8:
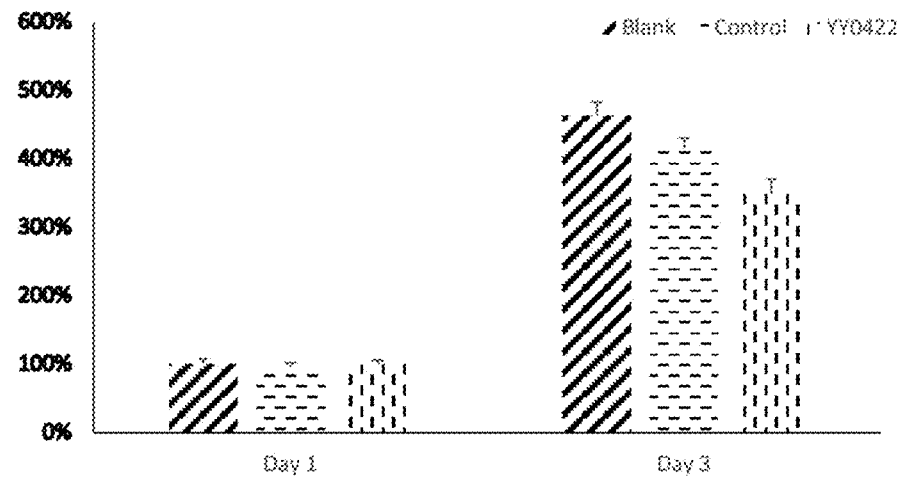

The killing results are shown in FIG. 8. From the results, it was clear that the bispecific antibodies YY0421 and YY0422 of the present invention, which target both human CD3 and CD20, can effectively mediate the killing of Daudi cells by T cells.

Example 7. Assay for Detecting Transplanted Tumors in Nude Mice $5\times10^7$ human Daudi cells in logarithmic growth stage with good morphology were injected subcutaneously into the anterior axilla of SPF grade BALB/C nude mice, and 10 μg each of PBMC cells ($2.5\times10^8$, purchased from ATCC (American Type Culture Collection)) and a bispecific antibody of the present invention or control antibody REGN1979, were injected on day 6 after injection. The maximum longitudinal diameter and maximum transverse diameter of the subcutaneous tumors were measured daily, the volume of the tumors was calculated, and the diet and body weight of the nude mice were observed and recorded. On day 28, all mice were executed by cervical dissection, and the tumors were then separated, photographed and weighed.

Figure 9:
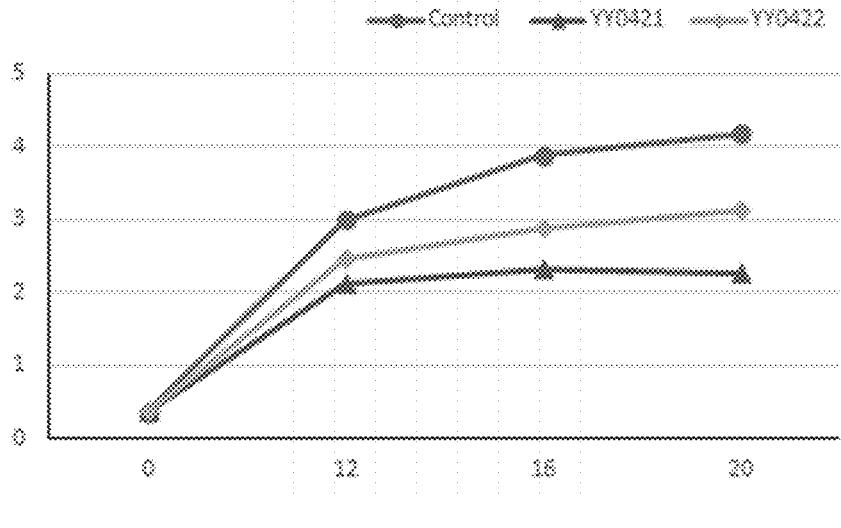
FIG. 9 shows the results of the inhibition of the growth of human Daudi cell-induced subcutaneous tumors in nude mice by the bispecific antibody of the present invention as well as the bispecific antibody REGN1979 as a control. The horizontal coordinate indicates the number of days and the vertical coordinate indicates the tumor volume (cubic millimeters).

The results of the assay for detecting transplanted tumors in nude mice are shown in FIG. 9. The results indicated that the bispecific antibody of the present invention targeting both human CD3 and CD20 had good biological activity and can significantly inhibit the proliferation of human Daudi cell-induced subcutaneous tumors in nude mice.

Some of the amino acid sequences mentioned herein are as follows.

```
YY0421 Amino acid sequence of the CD3-binding
moiety
                                    SEQ ID NO: 6
DIQLTQSPAIMSASPGEKVTMTCRASSSVSYMNWYQQKSGTSPKRWIYD

TSKVASGVPYRFSGSGSGTSYSLTISSMEAEDAATYYCQQWSSNPLTFG

AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGECGGGGSGGGGSGGGGSGGGGSGGGGSGGGGSGG

GGSGGGGSGGGGSGGGGSGGGGSGGGGSDIKLQQSGAELARPGASVKMS

CKTSGYTFTRYTMHWVKQRPGQGLEWIGYINPSRGYTNYNQKFKDKATL

TTDKSSSTAYMQLSSLTSEDSAVYYCARYYDDHYCLDYWGQGTTLTVSS

ASTKGPSVFPLAPCSRSTSESTAALGCLVKDYFPEPVTVSWNSGALTSG
```

```
VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPCQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLG

YY0421 Amino acid sequence of light chain of the
CD20-binding moiety
                                    SEQ ID NO: 7
EIVLTQSPATLSLSPGERATLSCRASQSVSSYLAWYQQKPGQAPRLLIY

DASNRATGIPARFSGSGSGTDFTLTISSLEPEDFAVYYCQQRSNWPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

YY0421 Amino acid sequence of heavy chain of the
CD20-binding moiety
                                    SEQ ID NO: 8
EVQLVESGGGLVQPGRSLRLSCAASGFTFNDYAMHWVRQAPGKGLEWVS

TISWNSGSIGYADSVKGRFTISRDNAKKSLYLQMNSLRAEDTALYYCAK

DIQYGNYYYGMDVWGQGTTVTVSSASTKGPSVFPLAPCSRSTSESTAAL

GCLVKDYFPEPVTVSWNSGALTSGVHTFPAVLQSSGLYSLSSVVTVPSS

SLGTKTYTCNVDHKPSNTKVDKRVESKYGPPCPPCPAPEFLGGPSVFLF

PPKPKDTLMISRTPEVTCVVVDVSQEDPEVQFNVVYVDGVEVHNAKTKP

REEQFNSTYRVVSVLTVLHQDWLNGKEYKCKVSNKGLPSSIEKTISKAK

GQPREPQVCTLPPSQEEMTKNQVSLSCAVKGFYPSDIAVEWESNGQPEN

NYKTTPPVLDSDGSFFLVSRLTVDKSRWQEGNVFSCSVMHEALHNHYTQ

KSLSLSLG

YY0422 Amino acid sequence of the CD3-binding
moiety
                                    SEQ ID NO: 9
DIQLTQSPAIMSASPGEKVTMTCRASSSVSYMNWYQQKSGTSPKRWIYD

TSKVASGVPYRFSGSGSGTSYSLTISSMEAEDAATYYCQQWSSNPLTFG

AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGECGGGGSGGGGSGGGGSGGGGSGGGGSGGGGSGG

GGSGGGGSGGGGSGGGGSGGGGSGGGGSDIKLQQSGAELARPGASVKMS

CKTSGYTFTRYTMHWVKQRPGQGLEWIGYINPSRGYTNYNQKFKDKATL

TTDKSSSTAYMQLSSLTSEDSAVYYCARYYDDHYCLDYWGQGTTLTVSS

ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPCQEEMTKNQVSL

WCLVKGFYPSDIAVEWESNGQPENNYKTTPPVLDSDGSFFLYSRLTVDK

SRWQEGNVFSCSVMHEALHNHYTQKSLSLSLG
```

-continued

YY0422 Amino acid sequence of the CD20-binding
moiety

SEQ ID NO: 10

EIVLTQSPATLSLSPGERATLSCRASQSVSSYLAWYQQKPGQAPRLLIY

DASNRATGIPARFSGSGSGTDFTLTISSLEPEDFAVYYCQQRSNWPITF

GQGTRLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGECGGGGSGGGGSGGGGSGGGGSGGGGSGGGGSG

GGGSGGGGSGGGGSGGGGSGGGGSGGGGSEVQLVESGGGLVQPGRSLRL

SCAASGFTFNDYAMHWVRQAPGKGLEWVSTISWNSGSIGYADSVKGRFT

ISRDNAKKSLYLQMNSLRAEDTALYYCAKDIQYGNYYYGMDVWGQGTTV

-continued

TVSSASTKGPSVFPLAPCSRSTSESTAALGCLVKDYFPEPVTVSWNSGA

LTSGVHTFPAVLQSSGLYSLSSVVTVPSSSLGTKTYTCNVDHKPSNTKV

DKRVESKYGPPCPPCPAPEFLGGPSVFLFPPKPKDTLMISRTPEVTCVV

VDVSQEDPEVQFNWYVDGVEVHNAKTKPREEQFNSTYRVVSVLTVLHQD

WLNGKEYKCKVSNKGLPSSIEKTISKAKGQPREPQVCTLPPSQEEMTKN

QVSLSCAVKGFYPSDIAVEWESNGQPENNYKTTPPVLDSDGSFFLVSRL

TVDKSRWQEGNVFSCSVMHEALHNHYTQKSLSLSLG

Tandemly repeated unit sequence

SEQ ID NO: 11

GGGGS

---

The invention claimed is:

1. An anti-CD3 single chain Fab molecule comprising a Fab light chain and a Fab heavy chain, wherein C-terminal of the Fab light chain is connected to N-terminal of the Fab heavy chain by a linking peptide having a length of 60 amino acids and the anti-CD3 single chain Fab molecule comprises an amino acid sequence as set forth in SEQ ID NO: 6 or 9.

2. An anti-CD20 single chain Fab molecule comprising a Fab light chain and a Fab heavy chain, wherein C-terminal of the Fab light chain is connected to N-terminal of the Fab heavy chain by a linking peptide having a length of 60 amino acids and the anti-CD20 single chain Fab molecule comprises an amino acid sequence as set forth in SEQ ID NO: 10.

* * * * *